US011219416B2

United States Patent
Wilson et al.

(10) Patent No.: US 11,219,416 B2
(45) Date of Patent: Jan. 11, 2022

(54) GRAPHICALLY DISPLAYING EVOKED POTENTIALS

(71) Applicant: Persyst Development Corporation, Solana Beach, CA (US)

(72) Inventors: Scott B. Wilson, Del Mar, CA (US); Mark L. Scheuer, Wexford, PA (US)

(73) Assignee: Persyst Development Corporation, Solana Beach, CA (US)

( * ) Notice: Subject to any disclaimer, the term of this patent is extended or adjusted under 35 U.S.C. 154(b) by 292 days.

(21) Appl. No.: 16/288,731

(22) Filed: Feb. 28, 2019

(65) Prior Publication Data

US 2019/0274637 A1 Sep. 12, 2019

Related U.S. Application Data

(60) Provisional application No. 62/641,665, filed on Mar. 12, 2018.

(51) Int. Cl.
*A61B 5/377* (2021.01)
*A61B 5/00* (2006.01)

(52) U.S. Cl.
CPC .............. *A61B 5/742* (2013.01); *A61B 5/377* (2021.01); *A61B 5/6803* (2013.01)

(58) Field of Classification Search
CPC ....... A61B 5/377; A61B 5/6803; A61B 5/369; A61B 5/383; A61B 5/4094; A61B 5/7203; A61B 5/7235; A61B 5/742

See application file for complete search history.

(56) References Cited

U.S. PATENT DOCUMENTS

| | | |
|---|---|---|
| RE30,502 E | 2/1981 | Lencioni, Jr. |
| 4,550,736 A | 11/1985 | Broughton et al. |
| 4,644,956 A | 2/1987 | Morgenstern |
| 4,709,702 A | 12/1987 | Sherwin |
| 4,936,306 A | 6/1990 | Doty |
| 4,967,038 A | 10/1990 | Gevins et al. |
| 5,038,782 A | 8/1991 | Gevins et al. |
| 5,230,344 A | 7/1993 | Ozdamar et al. |
| 5,230,346 A | 7/1993 | Leuchter et al. |
| 5,305,746 A | 4/1994 | Fendrock |
| 5,309,909 A | 5/1994 | Gadsby et al. |
| 5,626,145 A | 5/1997 | Clapp et al. |
| 5,730,146 A | 3/1998 | Itil et al. |
| 5,846,208 A | 12/1998 | Pichlmayr et al. |
| 5,983,128 A * | 11/1999 | Baudonniere ........ A61B 5/4863 600/544 |
| 6,224,549 B1 | 5/2001 | Drongelen |

(Continued)

OTHER PUBLICATIONS

Teplan, Fundamentals of EEG Measurement, Measurement Science Review, vol. 2, Section 2, 2002.

(Continued)

*Primary Examiner* — Navin Natnithithadha
(74) *Attorney, Agent, or Firm* — Clause Eight; Michael Catania (57) ABSTRACT

A method for graphically displaying evoked potentials is disclosed herein. The method transforms each of an averaged evoked potentials into a single vertical line, wherein a first amplitude range is represented by a first color, a second amplitude range is represented by a second color, a third amplitude range is represented by a third color and a fourth amplitude range is represented by a fourth color.

11 Claims, 7 Drawing Sheets

(56) References Cited

U.S. PATENT DOCUMENTS

| | | |
|---|---|---|
| 6,334,856 B1 | 1/2002 | Mien et al. |
| 6,493,576 B1 | 12/2002 | Dankwart-Eder |
| 6,591,132 B2 | 7/2003 | Gotman et al. |
| 6,735,467 B2 | 5/2004 | Wilson |
| 6,931,274 B2 | 8/2005 | Williams |
| 7,286,871 B2 | 10/2007 | Cohen |
| 7,754,190 B2 | 7/2010 | Suffin |
| 7,809,433 B2 | 10/2010 | Keenan |
| 7,904,144 B2 | 3/2011 | Causevic et al. |
| 7,941,201 B2 | 5/2011 | Chiou et al. |
| 8,112,141 B2 | 2/2012 | Wilson et al. |
| 8,155,736 B2 | 4/2012 | Sullivan et al. |
| 8,185,183 B1 | 5/2012 | Wilson et al. |
| 8,271,065 B1 | 9/2012 | Wilson et al. |
| 8,428,681 B2 | 4/2013 | Wilson et al. |
| 8,538,502 B1 | 9/2013 | Wilson et al. |
| 8,666,484 B2 | 3/2014 | Nierenberg et al. |
| 8,694,070 B2 | 4/2014 | Wilson |
| 8,972,001 B2 | 3/2015 | Nierenberg et al. |
| 9,055,927 B2 | 6/2015 | Wilson et al. |
| 9,232,922 B2 | 1/2016 | Wilson et al. |
| 10,022,291 B2 | 7/2018 | Wilson et al. |
| 10,105,091 B2 | 10/2018 | Papay et al. |
| 2002/0082551 A1 | 6/2002 | Ennen et al. |
| 2002/0099306 A1 | 7/2002 | Shaw et al. |
| 2003/0144601 A1 | 7/2003 | Prichep |
| 2004/0059241 A1 | 3/2004 | Suffin |
| 2004/0152957 A1 | 8/2004 | Stivoric et al. |
| 2005/0059874 A1 | 3/2005 | Fuchs et al. |
| 2005/0144042 A1 | 6/2005 | Joffe et al. |
| 2007/0135727 A1 | 6/2007 | Virtanen et al. |
| 2007/0167858 A1 | 7/2007 | Virtanen et al. |
| 2008/0027515 A1 | 1/2008 | Harris et al. |
| 2008/0262335 A1 | 10/2008 | Sun et al. |
| 2009/0062680 A1 | 3/2009 | Sandford |
| 2009/0247895 A1 | 10/2009 | Morikawa et al. |
| 2010/0098289 A1 | 4/2010 | Tognoli et al. |
| 2011/0015503 A1 | 1/2011 | Joffe et al. |
| 2011/0178421 A1 | 7/2011 | Schultz |
| 2011/0224569 A1 | 9/2011 | Isenhart et al. |
| 2014/0276194 A1* | 9/2014 | Osorio .................. A61B 5/377 |
| | | 600/554 |
| 2015/0112223 A1 | 4/2015 | Nierenberg et al. |
| 2015/0351654 A1 | 12/2015 | Kilsgaard et al. |
| 2016/0270679 A1* | 9/2016 | Mahon ................. A61N 1/0492 |
| 2018/0221644 A1* | 8/2018 | Grill ..................... A61N 1/378 |
| 2019/0239763 A1* | 8/2019 | Block ................... A61B 5/377 |
| 2020/0054888 A1* | 2/2020 | Etkin ................. A61B 5/7207 |

OTHER PUBLICATIONS

International Search Report for PCT Application PCT/US2019/020433, dated Jun. 13, 2019.

* cited by examiner

GRAPHICALLY DISPLAYING EVOKED POTENTIALS

CROSS REFERENCE TO RELATED APPLICATION

The Present Application claims priority to U.S. Provisional Patent Application No. 62/641,665, filed on Mar. 12, 2018, which is hereby incorporated by reference in its entirety.

STATEMENT REGARDING FEDERALLY SPONSORED RESEARCH OR DEVELOPMENT

Not Applicable

BACKGROUND OF THE INVENTION

Field of the Invention

The present invention generally relates to evoked potentials.

Description of the Related Art

An evoked potential measures the electrical activity of the brain in response to stimulation of specific sensory nerve pathways.

A sensory evoked potential uses short electrical impulses administered to an arm or a leg of a patient.

Evoked potential amplitudes tend to be low, ranging from less than a microvolt to several microvolts, compared to tens of microvolts for EEG, millivolts for EMG, and often close to a volt for ECG. To resolve these low-amplitude potentials against the background of ongoing EEG, ECG, EMG, and other biological signals and ambient noise, signal averaging is usually required. The signal is time-locked to the stimulus and most of the noise occurs randomly, allowing the noise to be averaged out with averaging of repeated responses.

Signals can be recorded from cerebral cortex, brain stem, spinal cord and peripheral nerves. Usually the term "evoked potential" is reserved for responses involving either recording from, or stimulation of, central nervous system structures. Thus evoked compound motor action potentials or sensory nerve action potentials as used in nerve conduction studies are generally not thought of as evoked potentials, though they do meet the above definition.

An electroencephalogram ("EEG") is a diagnostic tool that measures and records the electrical activity of a person's brain in order to evaluate cerebral functions. Multiple electrodes are attached to a person's head and connected to a machine by wires. The machine amplifies the signals and records the electrical activity of a person's brain. The electrical activity is produced by the summation of neural activity across a plurality of neurons. These neurons generate small electric voltage fields. The aggregate of these electric voltage fields create an electrical reading which electrodes on the person's head are able to detect and record. An EEG is a superposition of multiple simpler signals. In a normal adult, the amplitude of an EEG signal typically ranges from 1 micro-Volt to 100 micro-Volts, and the EEG signal is approximately 10 to 20 milli-Volts when measured with subdural electrodes. The monitoring of the amplitude and temporal dynamics of the electrical signals provides information about the underlying neural activity and medical conditions of the person.

An EEG is performed to: diagnose epilepsy; verify problems with loss of consciousness or dementia; verify brain activity for a person in a coma; study sleep disorders, monitor brain activity during surgery, and additional physical problems.

Multiple electrodes (typically 17-21, however there are standard positions for at least 70) are attached to a person's head during an EEG. The electrodes are referenced by the position of the electrode in relation to a lobe or area of a person's brain. The references are as follows: F=frontal; Fp=frontopolar; T=temporal; C=central; P=parietal; O=occipital; and A=auricular (ear electrode). Numerals are used to further narrow the position and "z" points relate to electrode sites in the midline of a person's head. An electrocardiogram ("EKG") may also appear on an EEG display.

The EEG records brain waves from different amplifiers using various combinations of electrodes called montages. Montages are generally created to provide a clear picture of the spatial distribution of the EEG across the cortex. A montage is an electrical map obtained from a spatial array of recording electrodes and preferably refers to a particular combination of electrodes examined at a particular point in time.

In bipolar montages, consecutive pairs of electrodes are linked by connecting the electrode input 2 of one channel to input 1 of the subsequent channel, so that adjacent channels have one electrode in common. The bipolar chains of electrodes may be connected going from front to back (longitudinal) or from left to right (transverse). In a bipolar montage signals between two active electrode sites are compared resulting in the difference in activity recorded. Another type of montage is the referential montage or monopolar montage. In a referential montage, various electrodes are connected to input 1 of each amplifier and a reference electrode is connected to input 2 of each amplifier. In a reference montage, signals are collected at an active electrode site and compared to a common reference electrode.

Reference montages are good for determining the true amplitude and morphology of a waveform. For temporal electrodes, CZ is usually a good scalp reference.

Being able to locate the origin of electrical activity ("localization") is critical to being able to analyze the EEG. Localization of normal or abnormal brain waves in bipolar montages is usually accomplished by identifying "phase reversal," a deflection of the two channels within a chain pointing to opposite directions. In a referential montage, all channels may show deflections in the same direction. If the electrical activity at the active electrodes is positive when compared to the activity at the reference electrode, the deflection will be downward. Electrodes where the electrical activity is the same as at the reference electrode will not show any deflection. In general, the electrode with the largest upward deflection represents the maximum negative activity in a referential montage.

Some patterns indicate a tendency toward seizures in a person. A physician may refer to these waves as "epileptiform abnormalities" or "epilepsy waves." These include spikes, sharp waves, and spike-and-wave discharges. Spikes and sharp waves in a specific area of the brain, such as the left temporal lobe, indicate that partial seizures might possibly come from that area. Primary generalized epilepsy, on the other hand, is suggested by spike-and-wave discharges that are widely spread over both hemispheres of the brain, especially if they begin in both hemispheres at the same time.

There are several types of brain waves: alpha waves, beta waves, delta wave, theta waves and gamma waves. Alpha waves have a frequency of 8 to 12 Hertz ("Hz"). Alpha waves are normally found when a person is relaxed or in a waking state when a person's eyes are closed but the person is mentally alert. Alpha waves cease when a person's eyes are open or the person is concentrating. Beta waves have a frequency of 13 Hz to 30 Hz. Beta waves are normally found when a person is alert, thinking, agitated, or has taken high doses of certain medicines. Delta waves have a frequency of less than 3 Hz. Delta waves are normally found only when a person is asleep (non-REM or dreamless sleep) or the person is a young child. Theta waves have a frequency of 4 Hz to 7 Hz. Theta waves are normally found only when the person is asleep (dream or REM sleep) or the person is a young child. Gamma waves have a frequency of 30 Hz to 100 Hz. Gamma waves are normally found during higher mental activity and motor functions.

The following definitions are used herein.

"Amplitude" refers to the vertical distance measured from the trough to the maximal peak (negative or positive). It expresses information about the size of the neuron population and its activation synchrony during the component generation.

The term "analogue to digital conversion" refers to when an analogue signal is converted into a digital signal which can then be stored in a computer for further processing. Analogue signals are "real world" signals (e.g., physiological signals such as electroencephalogram, electrocardiogram or electrooculogram). In order for them to be stored and manipulated by a computer, these signals must be converted into a discrete digital form the computer can understand.

"Artifacts" are electrical signals detected along the scalp by an EEG, but that originate from non-cerebral origin. There are patient related artifacts (e.g., movement, sweating, ECG, eye movements) and technical artifacts (50/60 Hz artifact, cable movements, electrode paste-related).

The term "differential amplifier" refers to the key to electrophysiological equipment. It magnifies the difference between two inputs (one amplifier per pair of electrodes).

"Duration" is the time interval from the beginning of the voltage change to its return to the baseline. It is also a measurement of the synchronous activation of neurons involved in the component generation.

"Electrode" refers to a conductor used to establish electrical contact with a nonmetallic part of a circuit. EEG electrodes are small metal discs usually made of stainless steel, tin, gold or silver covered with a silver chloride coating. They are placed on the scalp in special positions.

"Electrode gel" acts as a malleable extension of the electrode, so that the movement of the electrodes leads is less likely to produce artifacts. The gel maximizes skin contact and allows for a low-resistance recording through the skin.

The term "electrode positioning" (10/20 system) refers to the standardized placement of scalp electrodes for a classical EEG recording. The essence of this system is the distance in percentages of the 10/20 range between Nasion-Inion and fixed points. These points are marked as the Frontal pole (Fp), Central (C), Parietal (P), occipital (O), and Temporal (T). The midline electrodes are marked with a subscript z, which stands for zero. The odd numbers are used as subscript for points over the left hemisphere, and even numbers over the right "Electroencephalogram" or "EEG" refers to the tracing of brain waves, by recording the electrical activity of the brain from the scalp, made by an electroencephalograph.

"Electroencephalograph" refers to an apparatus for detecting and recording brain waves (also called encephalograph).

"Epileptiform" refers to resembling that of epilepsy.

"Evoked potential" is an electrical potential recorded from a nervous system of a human or other animal following presentation of a stimulus, as distinct from spontaneous potentials as detected by electroencephalography (EEG), electromyography (EMG), or other electrophysiologic recording method.

"Filtering" refers to a process that removes unwanted frequencies from a signal.

"Filters" are devices that alter the frequency composition of the signal.

"Montage" means the placement of the electrodes. The EEG can be monitored with either a bipolar montage or a referential one. Bipolar means that there are two electrodes per one channel, so there is a reference electrode for each channel. The referential montage means that there is a common reference electrode for all the channels.

"Morphology" refers to the shape of the waveform. The shape of a wave or an EEG pattern is determined by the frequencies that combine to make up the waveform and by their phase and voltage relationships. Wave patterns can be described as being: "Monomorphic". Distinct EEG activity appearing to be composed of one dominant activity. "Polymorphic". distinct EEG activity composed of multiple frequencies that combine to form a complex waveform. "Sinusoidal". Waves resembling sine waves. Monomorphic activity usually is sinusoidal. "Transient". An isolated wave or pattern that is distinctly different from background activity.

"Spike" refers to a transient with a pointed peak and a duration from 20 to under 70 msec.

The term "sharp wave" refers to a transient with a pointed peak and duration of 70-200 msec.

The term "neural network algorithms" refers to algorithms that identify sharp transients that have a high probability of being epileptiform abnormalities.

"Noise" refers to any unwanted signal that modifies the desired signal. It can have multiple sources.

"Periodicity" refers to the distribution of patterns or elements in time (e.g., the appearance of a particular EEG activity at more or less regular intervals). The activity may be generalized, focal or lateralized.

An EEG epoch is an amplitude of a EEG signal as a function of time and frequency.

As a technical matter, evoked potentials are generally views as the average of more than one hundred individual signals. Generally, the averages are presented a little more than thirty seconds apart. The amplitude and timing of the resulting signal indicates the health of the brain and nerve system between stimulus and the recording electrode. One is usually looking for changes relative to a baseline. It is difficult to visually display this information to a technician.

BRIEF SUMMARY OF THE INVENTION

The present invention provides a solution to presenting data for evoked potentials.

One aspect of the present invention is a method for graphically displaying evoked potentials. The method includes acquiring a plurality of brain electroencephalogram responses to pulses from an electrical stimulant source positioned on a patient's body, the plurality of responses read by an electrode on the patient's head. The method also includes averaging each set time period of the plurality of pulse responses to generate a plurality of averaged evoked potentials. The method also includes transforming each of the plurality of averaged evoked potentials into a single vertical line, wherein a first amplitude range is represented by a first color, a second amplitude range is represented by a second color, a third amplitude range is represented by a third color and a fourth amplitude range is represented by a fourth color. The method also includes displaying each single vertical line representing each of the plurality of averaged evoked potentials on a graph as an ordered time series, wherein each of the plurality of averaged evoked potentials is displayed as a graphical image.

Another aspect of the present invention is a method for graphically displaying evoked potentials. The method includes acquiring a plurality of brain electroencephalogram responses to pulses from an electrical stimulant source positioned on a patient's body, the plurality of responses read by an electrode on the patient's head. The method also includes averaging each set time period of the plurality of pulse responses to generate a plurality of averaged evoked potentials. The method also includes transforming each of the plurality of averaged evoked potentials into a single vertical line having a plurality of colored bands, wherein each colored band of the plurality of color bands represents a different amplitude of each of the plurality of evoked potentials. The method also includes displaying each single vertical line representing each of the plurality of averaged evoked potentials on a graph, wherein each of the plurality of averaged evoked potentials is graphically displayed on a graph.

Another aspect of the present invention is a non-transitory computer-readable medium that stores a program that causes a processor to perform functions to graphically display evoked potentials by executing the following steps. The steps include acquiring a plurality of brain electroencephalogram responses to pulses from an electrical stimulant source positioned on a patient's body, the plurality of responses read by an electrode on the patient's head. The steps also include averaging each set time period of the plurality of pulse responses to generate a plurality of averaged evoked potentials. The steps also include transforming each of the plurality of averaged evoked potentials into a single vertical line having a plurality of colored bands, wherein each colored band of the plurality of color bands represents a different amplitude of each of the plurality of evoked potentials. The steps also include displaying each single vertical line representing each of the plurality of averaged evoked potentials on a graph, wherein each of the plurality of averaged evoked potentials is graphically displayed on a graph.

Having briefly described the present invention, the above and further objects, features and advantages thereof will be recognized by those skilled in the pertinent art from the following detailed description of the invention when taken in conjunction with the accompanying drawings.

DETAILED DESCRIPTION OF THE INVENTION

Figure 1:
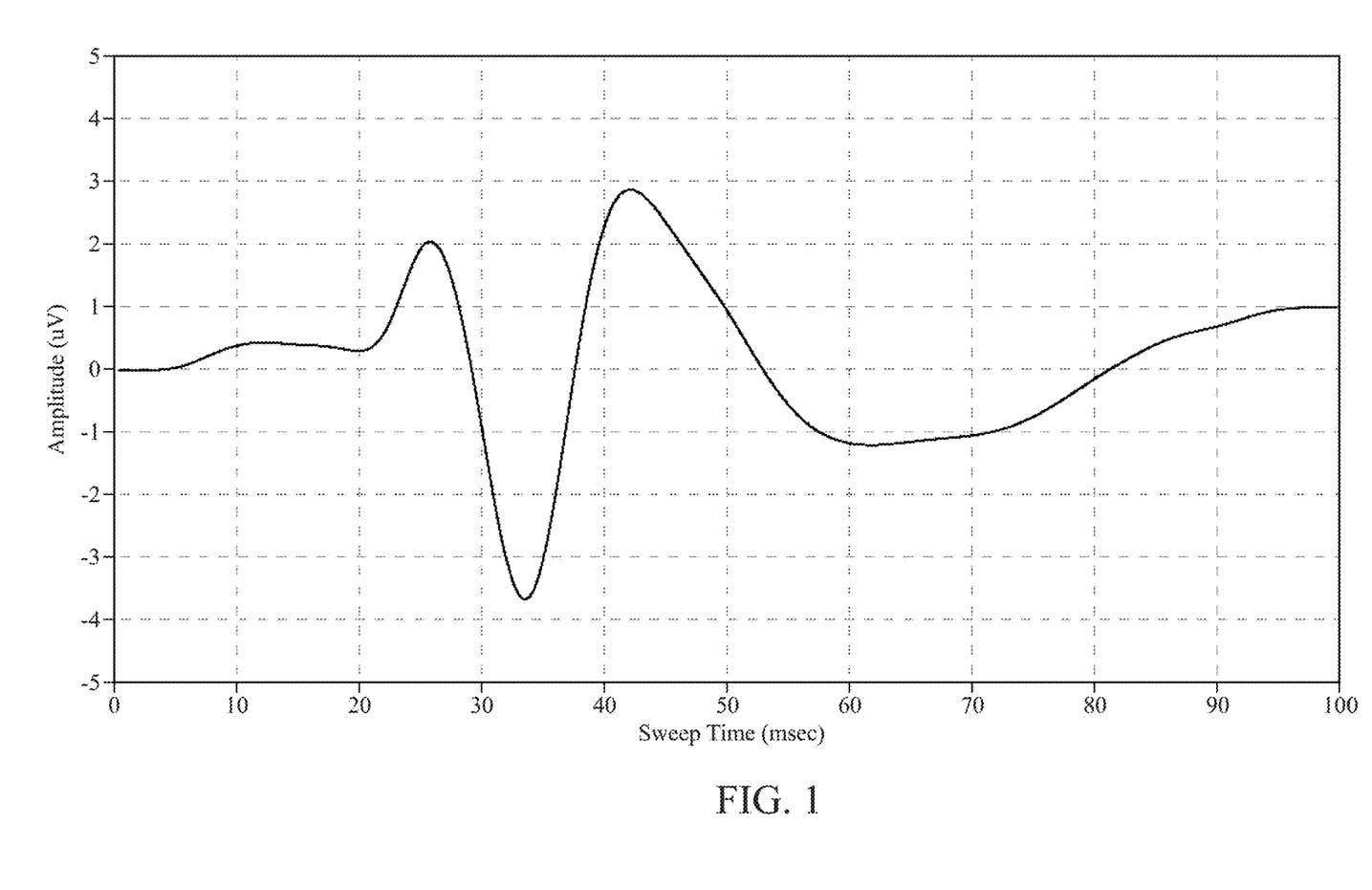
FIG. 1 is a graph of a single average evoked potential with amplitude on the Y-axis and time on the X-axis.

FIG. 1 illustrates an image of a graph of a single average evoked potential over a 100 millisecond period with an amplitude on the Y-axis and time on the X-axis. Evoked potentials are generally viewed as the average of more than one hundred individual signals. This removes background noise. Generally the averages are presented a little more than 30 seconds apart. The amplitude and time on the resulting signal indicates the health of the brain and nerve system between the stimulus and the recording electrode. In FIG. 1, the 0 time on the axis is the tie of the stimulus so all of the responses are aligned by the stimulus time for the average.

Figure 2:
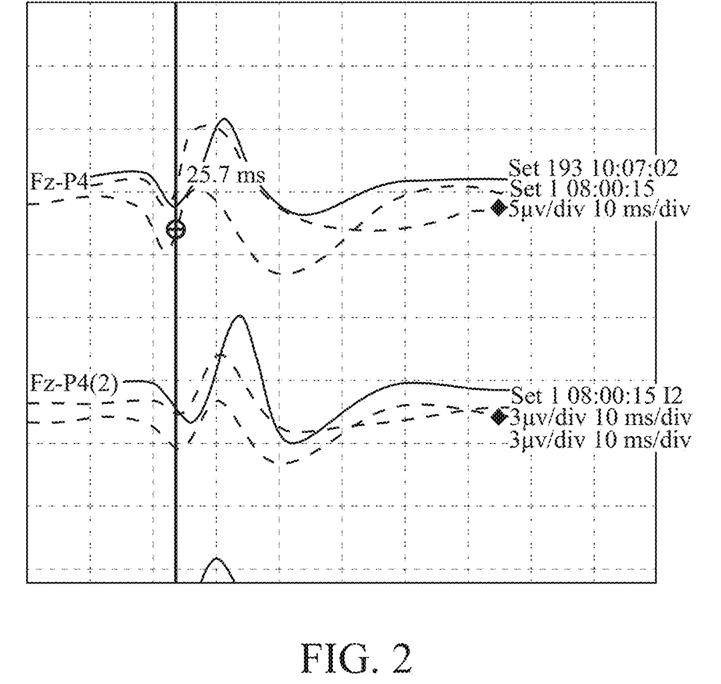
FIG. 2 is a graph of evoked potential waveforms.
Figure 2A:
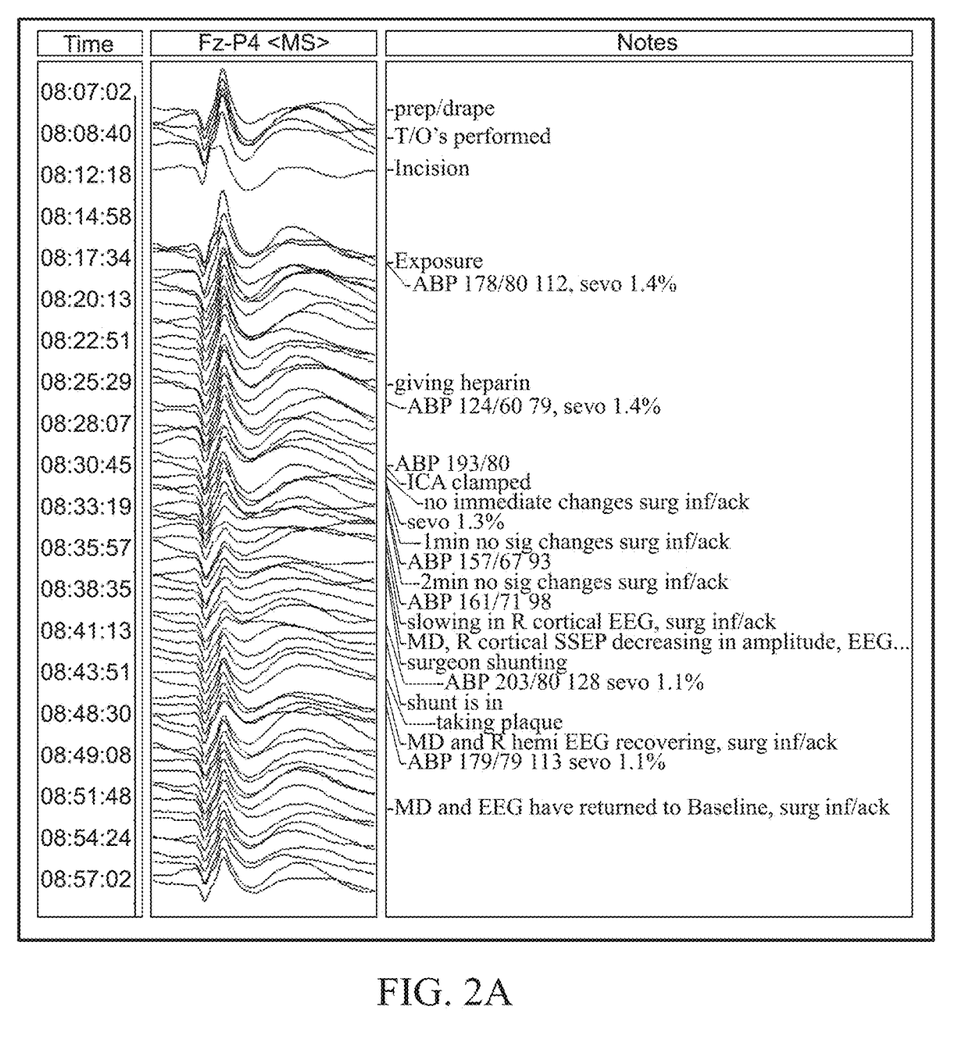
FIG. 2A is an illustration of evoked potentials showing each individual averaged evoked potential.

FIG. 2 is a graph of evoked potential waveforms. FIG. 2A is an illustration of evoked potentials showing each individual averaged evoked potential. Since one is looking for changes over time, the prior art systems that present these show a time series and display as shown in FIGS. 2 and 2A. In the middle of FIG. 2A, time is on the vertical axis, time is on the horizontal axis, and each individual average is shown. FIG. 2 shows selected waveforms with the ability to perform measurements to see if there are any changes. This is all done in real-time with the idea of providing feedback to a surgeon about changes. It can also be used at intervals in an intensive care to look for changes.

Figure 3:
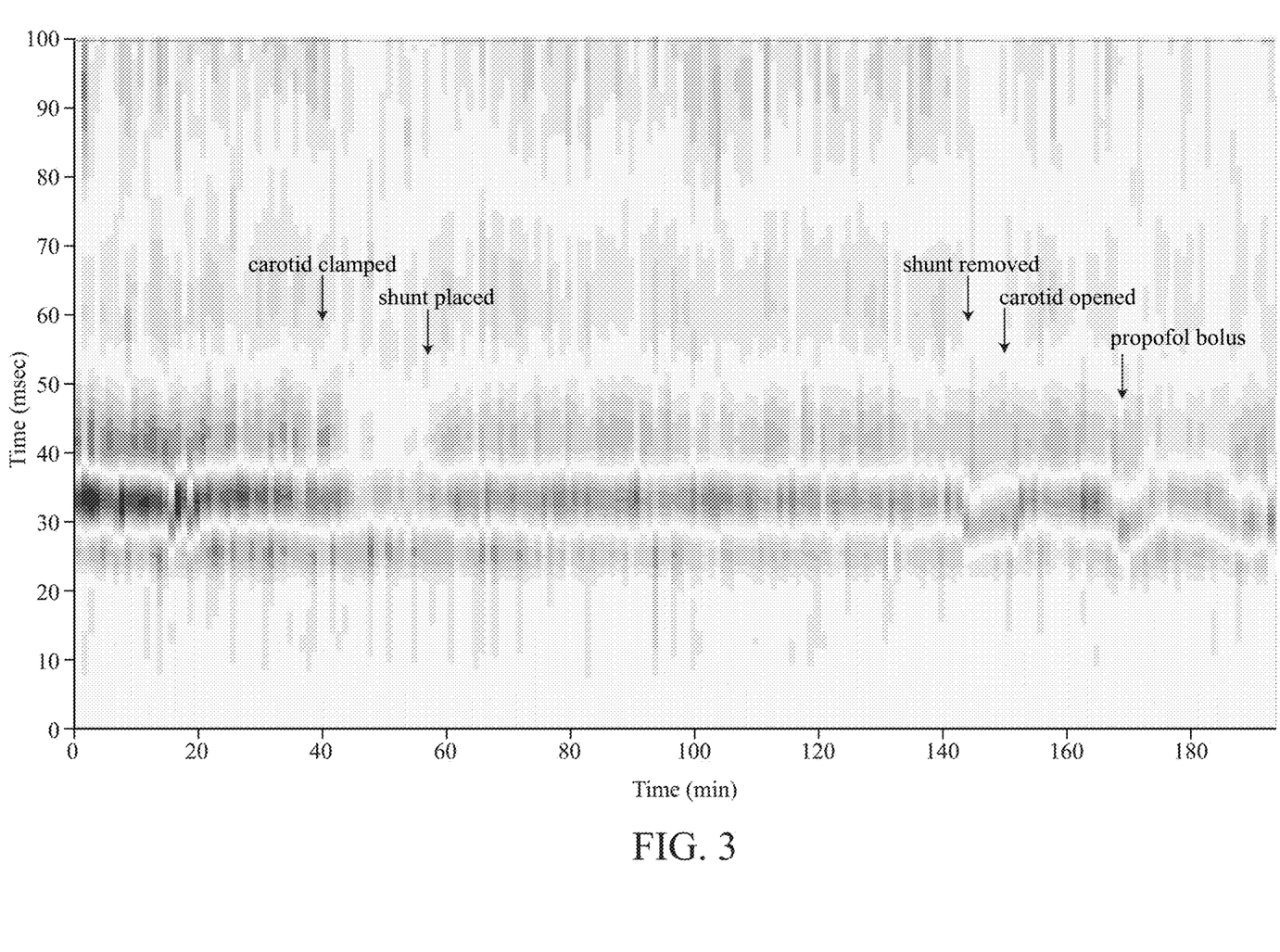
FIG. 3 is a display of the present invention showing averaged evoked potentials with time on the X-axis and the Y-axis and the amplitude shown in color.

FIG. 3 is a display of the present invention showing averaged evoked potentials with time in minutes on the X-axis, time in milliseconds on the Y-axis and the amplitude shown in color. The graph preferably has a Y-axis of milliseconds and an X-axis of minutes. The graph preferably has a Y axis generally scaled to a duration of the response from the evoked potentials and the X axis is scaled based on the length of the patient record. Each of the averaged evoked potentials is transformed into a single vertical line. A first amplitude range is represented by a first color, a second amplitude range is represented by a second color, a third amplitude range is represented by a third color, a fourth amplitude range is represented by a fourth color, a fifth amplitude range represented by a fifth color, and a sixth amplitude range represented by a sixth color. For example, in one embodiment, the first color is orange, the second color is blue, the third color is red, and fourth color is green and the fifth color is yellow. The peaks and troughs show up as color bands. The bands move higher and lower on the y-axis depending on the timing and the color indicates amplitude. Thus, it is easier for a surgeon, or other, to see changes, and an empirical null can be applied so that changes become scaled. The timing of the actual averages is not absolutely regular, and some may drop out due to an artifact or like event. So preferably the timing of the actual averages are placed correctly on the horizontal axis, and potentially provide interpolation. The chart is preferably updated in real-time. In an intensive care unit, it would be preferably to perform continuous evoked potentials and provide immediate indications whens changes start to occur.

The electrical stimulant source is preferably positioned on an arm of the patient's body. The electrical stimulant source is alternatively positioned on an ankle of the patient's body.

The set time period is approximately thirty seconds.

Each of the plurality of averaged evoked potentials is preferably representative of approximately one hundred pulses of the plurality of pulses.

Each band of color preferably adjusts on a Y-axis of the graph based on the timing.

Each band of color represents an amplitude range. For example, FIG. 1 shows a single average evoked potential over a 100 millisecond period with an amplitude that ranges from approximately −3.5 milli-Volts to approximately 3 milli-Volts. In one embodiment, a first color for a first amplitude band could represent a range from −3.5 milli-Volts to −2 milli-Volts, a second color for a second amplitude band could represent a range from −2.0 milli-Volts to 0 milli-Volts, a third color for a third amplitude band could represent a range from 0 milli-Volts to 1.5 milli-Volts, and a fourth color for a fourth amplitude band could represent a range from 1.5 milli-Volts to 3 milli-Volts. Moving from 0 millisecond to 100 milli-seconds, the color scheme would proceed from second color to the third color to the second color to the first color to the second color to the third color to the fourth color to the third color to the second color and finally to the third color. Those skilled in the pertinent art will recognize that the color scheme may be partitioned in many more colors depending on the size of the amplitude range.

Figure 4:
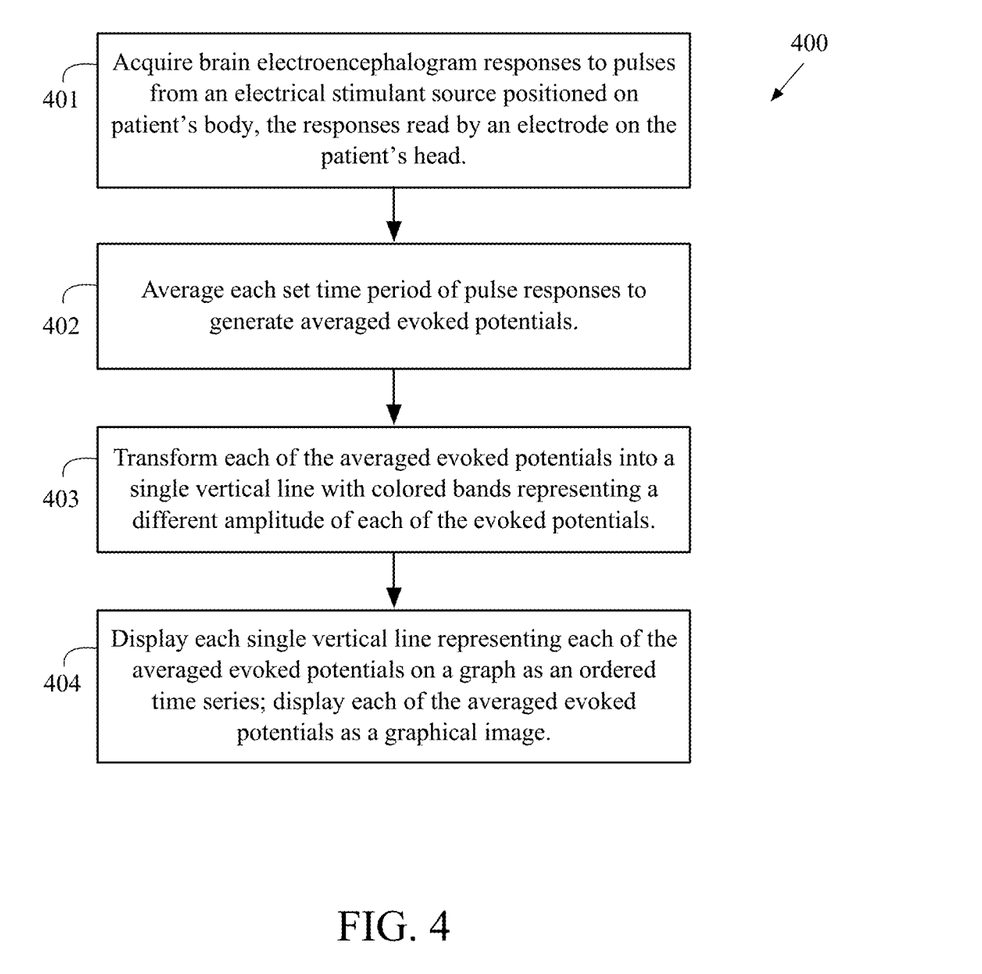
FIG. 4 is a flow chart for a method for graphically displaying evoked potentials.

A method 400 for graphically displaying evoked potentials is shown in FIG. 4. At block 401, multiple brain electroencephalogram responses are acquired to pulses from an electrical stimulant source positioned on a patient's body. The responses are read by an electrode on the patient's head. At block 402, each set time period of the pulse responses are averaged to generate a plurality of averaged evoked potentials. At block 403, each of the averaged evoked potentials is transformed into a single vertical line, wherein a first amplitude range is represented by a first color, a second amplitude range is represented by a second color, a third amplitude range is represented by a third color and a fourth amplitude range is represented by a fourth color. At block 404, each single vertical line representing each of the plurality of averaged evoked potentials is displayed on a graph as an ordered time series, wherein each of the plurality of averaged evoked potentials is displayed as a graphical image.

Figure 5:
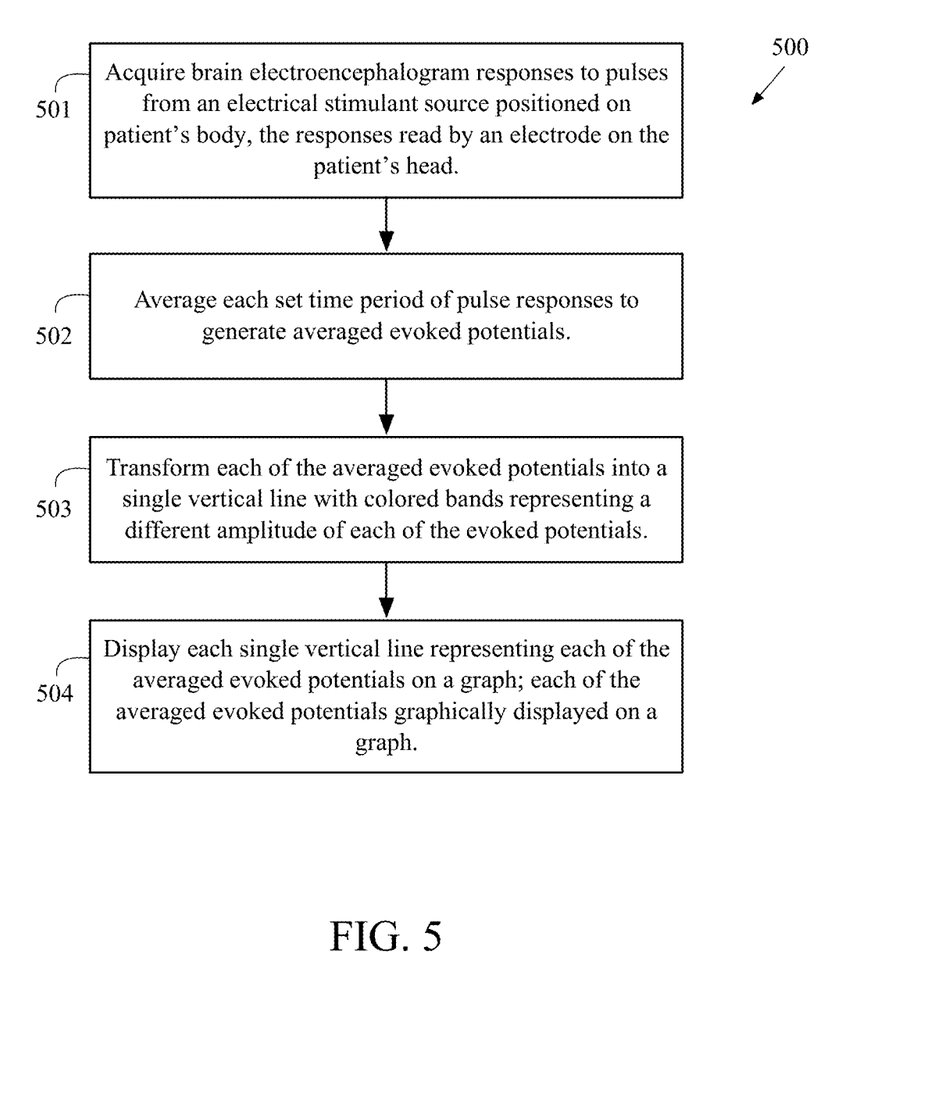
FIG. 5 is a flow chart for a method for graphically displaying evoked potentials.

Another method 500 for graphically displaying evoked potentials. At block 501, brain electroencephalogram responses to pulses from an electrical stimulant source positioned on a patient's body are acquired. The responses are read by an electrode on the patient's head. At block 502, each set time period of the pulse responses is averaged to generate a plurality of averaged evoked potentials. At block 503, each of the averaged evoked potentials is transformed into a single vertical line having a plurality of colored bands, wherein each colored band of the plurality of color bands represents a different amplitude of each of the plurality of evoked potentials. At block 504, each single vertical line representing each of the averaged evoked potentials is displayed on a graph, wherein each of the plurality of averaged evoked potentials is graphically displayed on a graph.

Figure 6:
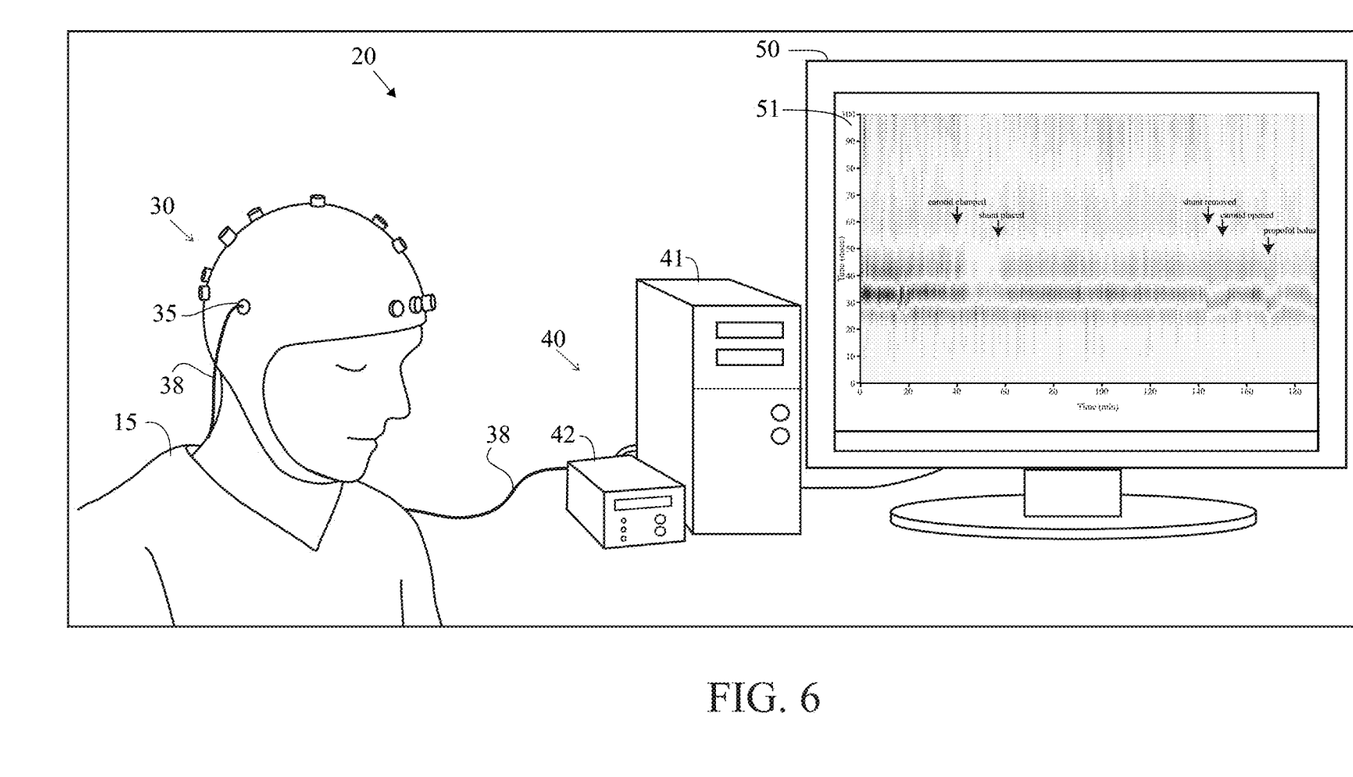
FIG. 6 is an illustration of obtaining an evoked potential from a patient.

FIG. 6 is an illustration of obtaining an evoked potential from a patient. A system 20 for obtaining an evoked potential from a patient is shown in FIG. 6. A patient 15 wears an electrode cap 30, consisting of a plurality of electrodes 35 attached to the patient's head with wires 38 from the electrodes 35 connected to an EEG machine component 40 which consists of an amplifier 42 for amplifying the signal to a computer 41 with a processor, which is used to analyze the signals from the electrodes 35 and generate a display of averaged evoked potentials wherein each of the averaged evoked potentials is transformed into a single vertical line having a plurality of colored bands, wherein each colored band of the plurality of color bands represents a different amplitude of each of the plurality of evoked potentials, which can be viewed on a screen 50. The processor of the computer 41 comprises a non-transitory computer-readable medium that stores a program that causes the processor to perform functions to graphically display evoked potentials by executing the following steps: acquiring a plurality of brain electroencephalogram responses to pulses from an electrical stimulant source positioned on a patient's body, the plurality of responses read by an electrode on the patient's head; averaging each set time period of the plurality of pulse responses to generate a plurality of averaged evoked potentials; transforming each of the plurality of averaged evoked potentials into a single vertical line having a plurality of colored bands, wherein each colored band of the plurality of color bands represents a different amplitude of each of the plurality of evoked potentials; and displaying each single vertical line representing each of the plurality of averaged evoked potentials on a graph, wherein each of the plurality of averaged evoked potentials is graphically displayed on a graph.

A more thorough description of an electrode utilized with the present invention is detailed in Wilson et al., U.S. Pat. No. 8,112,141 for a *Method And Device For Quick Press On EEG Electrode*, which is hereby incorporated by reference in its entirety. The EEG is optimized for automated artifact filtering. The EEG recordings are then processed using neural network algorithms to generate a processed EEG recording which is used to generate a qEEG.

An additional description of analyzing EEG recordings is set forth in Wilson et al., U.S. patent application Ser. No. 13/620,855, filed on Sep. 15, 2012, for a *Method And System For Analyzing An EEG Recording*, which is hereby incorporated by reference in its entirety.

A patient has a plurality of electrodes attached to the patient's head with wires from the electrodes connected to an amplifier for amplifying the signal to a processor, which is used to analyze the signals from the electrodes and create an EEG recording. The brain produces different signals at different points on a patient's head. Multiple electrodes are positioned on a patient's head. The CZ site is in the center. The number of electrodes determines the number of channels for an EEG. A greater number of channels produce a more detailed representation of a patient's brain activity. If an electrode is open, then the recording for the channel is inaccurate thereby generating false readings. Preferably, each amplifier 42 of an EEG machine component 40 corresponds to two electrodes 35 attached to a head of the patient 15. The output from an EEG machine component 40 is the difference in electrical activity detected by the two electrodes. The placement of each electrode is critical for an EEG report since the closer the electrode pairs are to each other, the less difference in the brainwaves that are recorded by the EEG machine component 40. A more thorough description of an electrode utilized with the present invention is detailed in Wilson et al., U.S. Pat. No. 8,112,141 for a *Method And Device For Quick Press On EEG Electrode*, which is hereby incorporated by reference in its entirety.

A more thorough description of EEG analysis utilized with the present invention is detailed in Wilson et al., U.S. patent application Ser. No. 13/620,855, filed on Sep. 15, 2012, for a *Method And System For Analyzing An EEG Recording*, which is hereby incorporated by reference in its entirety. A more thorough description of a user interface utilized with the present invention is detailed in Wilson et al., U.S. Pat. No. 9,055,927, for a *User Interface For Artifact Removal In An EEG*, which is hereby incorporated by reference in its entirety. An additional description of analyzing EEG recordings is set forth in Wilson et al., U.S. patent application Ser. No. 13/684,556, filed on Nov. 25, 2012, for a *Method And System For Detecting And Removing EEG Artifacts*, which is hereby incorporated by reference in its entirety. A more thorough description of displaying an EEG utilized with the present invention is detailed in Nierenberg et al., U.S. Pat. No. 8,666,484, for a *Method And System For Displaying EEG Recordings*, which is hereby incorporated by reference in its entirety. A more thorough description of displaying EEG recordings utilized with the present invention is detailed in Wilson et al., U.S. Pat. No. 9,232,922, for a *User Interface For Artifact Removal In An EEG*, which is hereby incorporated by reference in its entirety. An additional description of qEEG is set forth in Nierenberg et al., U.S. patent application Ser. No. 13/830,742, filed on Mar. 14, 2013, for a *Method And System To Calculate qEEG*, which is hereby incorporated by reference in its entirety. An additional description of using neural networks with the present invention is set forth in Wilson, U.S. patent application Ser. No. 14/078,497, filed on Nov. 12, 2013, for a *Method And System Training A Neural Network*, which is hereby incorporated by reference in its entirety. An additional description of using neural networks with the present invention is set forth in Nierenberg et al., U.S. patent application Ser. No. 14/222,655, filed on Jan. 20, 2014, for a *System And Method For Generating A Probability Value For An Event*, which is hereby incorporated by reference in its entirety. Wilson et al., U.S. patent application Ser. No. 15/131,216, filed on Apr. 18, 2016, which is hereby incorporated by reference in its entirety.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

We claim as our invention:

1. A method for graphically displaying evoked potentials in real-time to provide immediate indications when changes start to occur in a patient, the method comprising:

acquiring, at a processor in real-time, a plurality of brain electroencephalogram responses to pulses from an electrical stimulant source positioned on a patient's body, the plurality of brain electroencephalogram responses read by an electrode on the patient's head, each of the plurality of brain electroencephalogram responses having a set time period;

averaging, at the processor, each set time period of the plurality of brain electroencephalogram pulse responses to generate a plurality of averaged evoked potentials;

transforming, at the processor, each of the plurality of averaged evoked potentials into a single vertical line, wherein a first amplitude range is represented by a first color band, a second amplitude range is represented by a second color band, a third amplitude range is represented by a third color band and a fourth amplitude range is represented by a fourth color band, wherein each single vertical line has multiple colored bands, wherein each band of color adjusts on a Y-axis of the graph based on the timing; and displaying on a screen, each single vertical line representing each of the plurality of averaged evoked potentials on a graph as an ordered time series, wherein each of the plurality of averaged evoked potentials is displayed as a graphical image, wherein the graph has a Y-axis of milliseconds scaled to a duration of the response from the evoked potentials and an X-axis of minutes scaled based on a length of a patient record.

2. The method according to claim 1 further comprising a fifth amplitude range represented by a fifth color band, and a sixth amplitude range represented by a sixth color band.

3. The method according to claim 1 wherein the electrical stimulant source is positioned on an ankle of the patient's body.

4. The method according to claim 1 wherein the electrical stimulant source is positioned on an arm of the patient's body.

5. The method according to claim 1 wherein the set time period is thirty seconds.

6. The method according to claim 1 wherein the each of the plurality of averaged evoked potentials is representative of one hundred pulses of the plurality of pulses.

7. A method for graphically displaying evoked potentials in real-time to provide immediate indications when changes start to occur in a patient, the method comprising:

acquiring, at a processor in real-time, a plurality of brain electroencephalogram responses to pulses from an electrical stimulant source positioned on a patient's body, the plurality of brain electroencephalogram responses read by an electrode on the patient's head, each of the plurality of brain electroencephalogram responses having a set time period;

averaging, at the processor, each set time period of the plurality of brain electroencephalogram responses to generate a plurality of averaged evoked potentials;

transforming, at the processor, each of the plurality of averaged evoked potentials into a single vertical line having a plurality of colored bands, wherein each colored band of the plurality of color bands represents a different amplitude of each of the plurality of evoked potentials, wherein each band of color adjusts on a Y-axis of the graph based on the set time period; and displaying on a screen, each single vertical line representing each of the plurality of averaged evoked potentials on a graph, wherein each of the plurality of averaged evoked potentials is graphically displayed on the graph, wherein the graph has a Y-axis of milliseconds scaled to a duration of the response from the evoked potentials and an X-axis of minutes scaled based on a length of a patient record.

8. The method according to claim 7 wherein the electrical stimulant source is positioned on an ankle of the patient's body.

9. The method according to claim 7 wherein the electrical stimulant source is positioned on an arm of the patient's body.

10. The method according to claim 7 wherein the set time period is thirty seconds.

11. The method according to claim 7 wherein the each of the plurality of averaged evoked potentials is representative of one hundred pulses of the plurality of pulses.

\* \* \* \* \*